(12) United States Patent
Okada

(10) Patent No.: US 7,371,236 B2
(45) Date of Patent: May 13, 2008

(54) DIATHERMIC CUTTER

(75) Inventor: Tsutomu Okada, Tachikawa (JP)

(73) Assignee: Olympus Corporation, Tokyo (JP)

( * ) Notice: Subject to any disclaimer, the term of this patent is extended or adjusted under 35 U.S.C. 154(b) by 194 days.

(21) Appl. No.: 10/718,189

(22) Filed: Nov. 20, 2003

(65) Prior Publication Data

US 2004/0210215 A1 Oct. 21, 2004

(30) Foreign Application Priority Data

Nov. 21, 2002 (JP) ............................. 2002-338317

(51) Int. Cl.
*A61B 18/18* (2006.01)

(52) U.S. Cl. ...................................................... 606/45

(58) Field of Classification Search ............. 606/27–52
See application file for complete search history.

(56) References Cited

U.S. PATENT DOCUMENTS

| 1,908,583 | A | * | 5/1933 | Wappler | 606/49 |
| 4,503,855 | A | * | 3/1985 | Maslanka | 606/47 |
| 5,085,659 | A | * | 2/1992 | Rydell | 606/47 |
| 5,171,255 | A | * | 12/1992 | Rydell | 606/170 |
| 5,366,463 | A | * | 11/1994 | Ryan | 606/159 |
| 5,846,241 | A | * | 12/1998 | Kittur et al. | 606/48 |
| 6,190,384 | B1 | * | 2/2001 | Ouchi | 606/47 |

FOREIGN PATENT DOCUMENTS

| JP | 4-329944 | 11/1992 |
| JP | 8-299355 | 11/1996 |
| JP | 2002-301088 | 10/2002 |

OTHER PUBLICATIONS

T. Oyama et al., "Endoscopic Mucosal Resection Using a Hooking Knife (Hooking EMR)", Stomach and Intestine, (Tokyo), vol. 37, No. 9, 2002, pp. 1155-1161, together with English translation.
H. Inoue et al., "Endoscopic mucosal resection with a cap-fitted panendoscope for esophagus, stomach, and colon mucosal lesions", Gastointest. Endosc. 39: 58-62 1993 vol. 14, No. 9, together with English translation.

* cited by examiner

Primary Examiner—Roy D. Gibson
Assistant Examiner—Pete Vrettakos
(74) Attorney, Agent, or Firm—Scully, Scott, Murphy & Presser, P.C.

(57) ABSTRACT

There is disclosed a diathermic cutter including a cylindrical main body member having a central axis, an axially elongated member including a tip end portion movable so as to change a projected state from a tip end of the main body member along the central axis of the main body member, an electrode including a base end portion on which the tip end portion of the elongated member is disposed and extending in a direction deviating from the central axis of the elongated member, and an electrically insulating member with which the electrode is coated in such a manner that at least a part of a base-end surface of the base end portion of the electrode in the vicinity of the tip end of the main body member is exposed toward the tip end of the main body member.

2 Claims, 8 Drawing Sheets

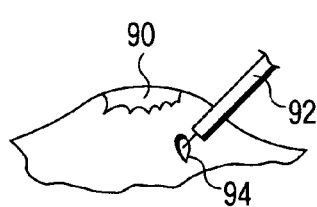
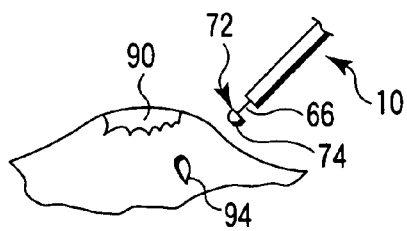
FIG. 2A  FIG. 2B
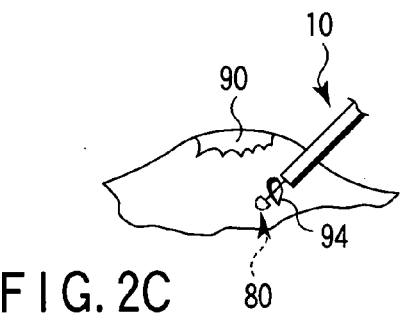
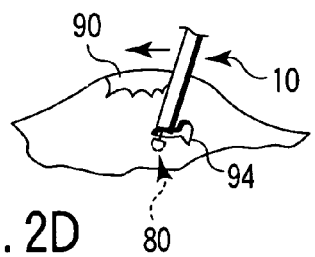
FIG. 2C  FIG. 2D
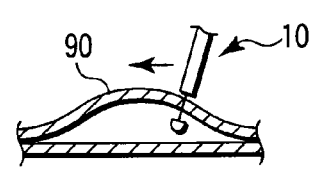
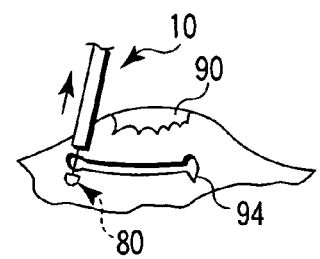
FIG. 2E  FIG. 2F
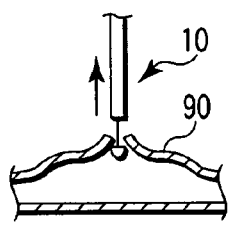
FIG. 2G
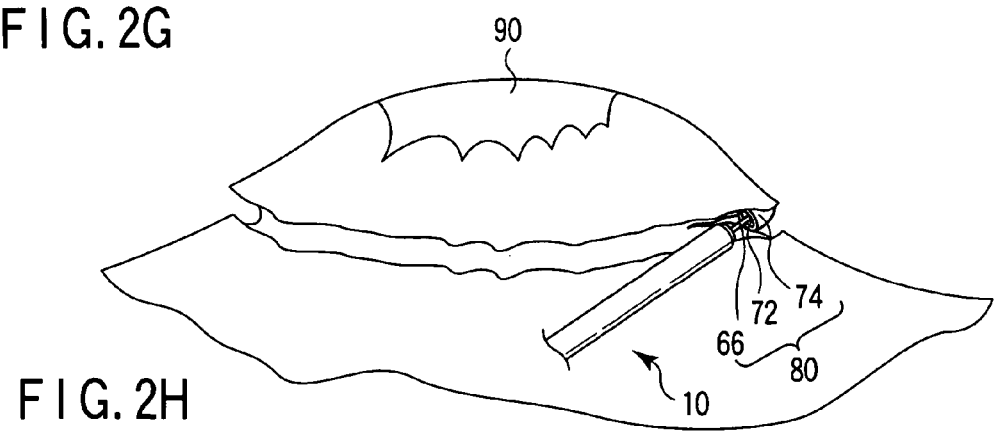
FIG. 2H

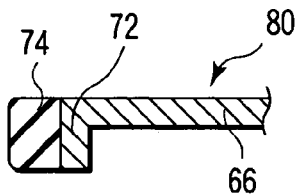
FIG. 7A
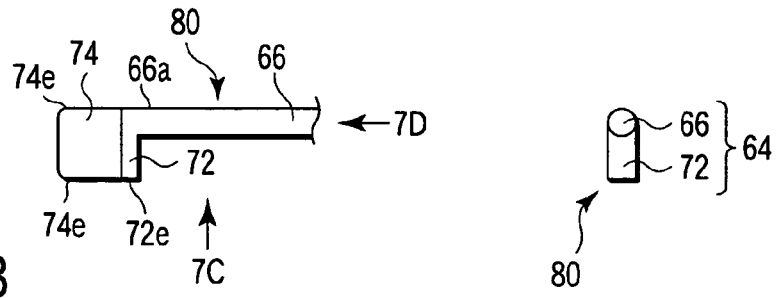
FIG. 7B
FIG. 7D
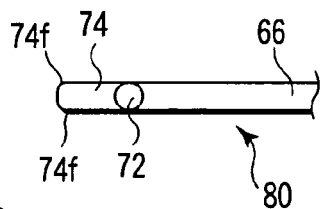
FIG. 7C
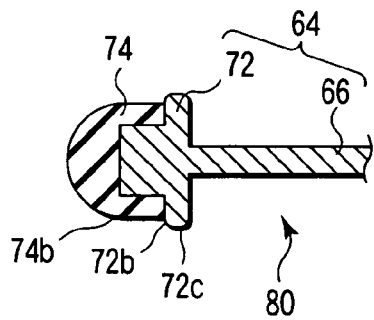
FIG. 8A
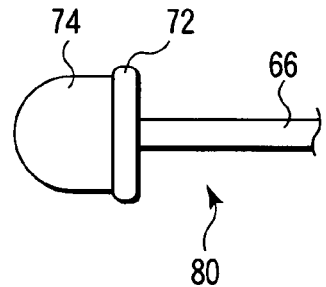
FIG. 8B

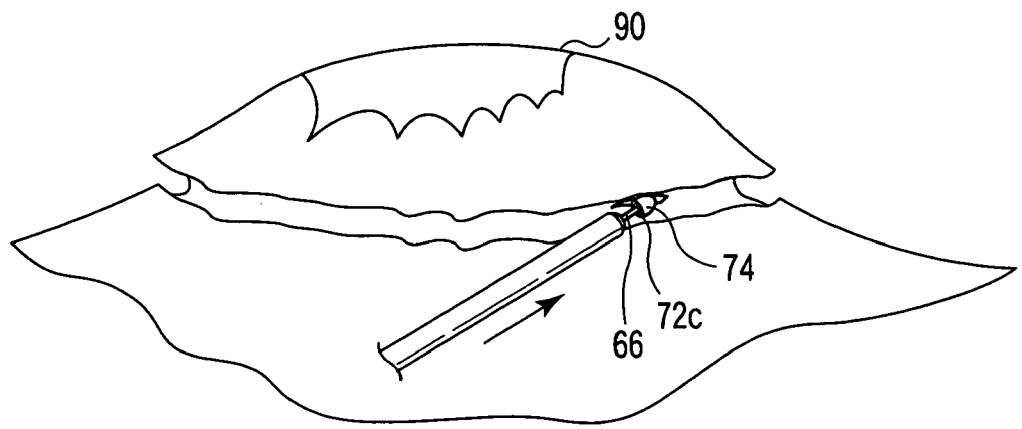
FIG. 9
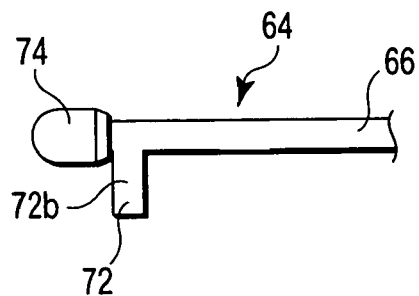
FIG. 10
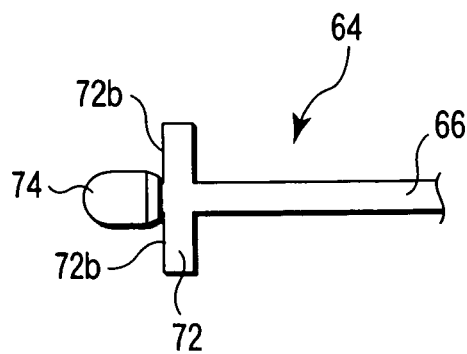 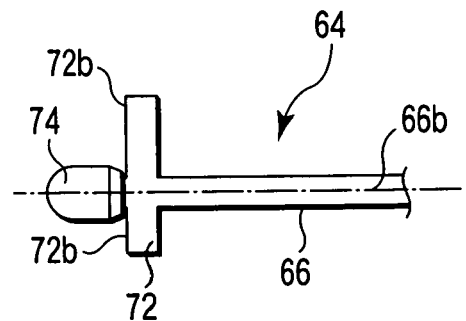
FIG. 11A              FIG. 11B

DIATHERMIC CUTTER

CROSS-REFERENCE TO RELATED APPLICATIONS

This application is based upon and claims the benefit of priority from the prior Japanese Patent Application No. 2002-338317, filed Nov. 21, 2002, the entire contents of which are incorporated herein by reference.

BACKGROUND OF THE INVENTION

1. Field of the Invention

The present invention relates to a diathermic cutter for cutting off living tissues.

2. Description of the Related Art

A treatment for cutting off living tissues such as mucosa, for example, via an endoscope has heretofore been carried out. A high-frequency treatment instrument disclosed, for example, in Jpn. Pat. Appln. KOKAI Publication No. 4-329944 is used in this cut-off treatment.

The high-frequency treatment instrument disclosed in Jpn. Pat. Appln. KOKAI Publication No. 4-329944 includes a needle-shaped cutter section (electrode section) extending in an axial direction. When a high-frequency current is supplied to this cutter section, the living tissue contacting the cutter section is cauterized/incised.

BRIEF SUMMARY OF THE INVENTION

According to one aspect of the present invention, there is provided a diathermic cutter including: a cylindrical main body member having a central axis; an elongated member which has a tip end portion projected from a tip end of the main body member and which is movably inserted in the main body member; an electrode disposed on the tip end portion of the elongated member and extended in a direction deviating from the central axis of the elongated member; and an electrically insulating member with which the electrode is coated in such a manner that at least a part of a base-end surface of the electrode disposed opposite to the tip end portion of the main body member is exposed.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a schematic diagram showing that initial incision is carried out to make a hole in a part of mucosa in a raised state of a lesion mucosa portion;

FIG. 2B is a schematic diagram showing that the diathermic cutter according to the first embodiment is endoscopically introduced and the cutter section is disposed in the vicinity of the lesion mucosa portion;

FIG. 2C is a schematic diagram showing that the cutter section of the diathermic cutter according to the first embodiment is inserted in an initially incised hole;

FIG. 2D is a schematic diagram showing that a high-frequency current is supplied to an electrode of the cutter section of the diathermic cutter according to the first embodiment, while the cutter section is moved along a predetermined cut-off direction;

FIG. 2E is a schematic diagram showing that the high-frequency current is supplied to the electrode of the cutter section of the diathermic cutter according to the first embodiment, while the cutter section is moved along the predetermined cut-off direction;

FIG. 2F is a schematic diagram showing that the high-frequency current is supplied to the electrode of the cutter section of the diathermic cutter according to the first embodiment, while the cutter section is moved along an axial direction of a small-diameter electrode section;

FIG. 2G is a schematic diagram showing that the high-frequency current is supplied to the electrode of the cutter section of the diathermic cutter according to the first embodiment, while the cutter section is moved along the axial direction (vertical direction) of the small-diameter electrode section;

FIG. 2H is a schematic diagram showing that a base end surface of a large-diameter electrode section and the small-diameter electrode section abut on a cut area obtained by incising a periphery of the lesion mucosa portion and that movement of a transverse direction is combined with that of a vertical direction of the diathermic cutter according to the first embodiment to successively cut open and peel the lesion mucosa portion by the small and large-diameter electrode sections;

FIG. 7A is a schematic sectional view of the cutter section in the diathermic cutter according to a sixth embodiment;

FIG. 7B is a schematic diagram of the cutter section in the diathermic cutter according to the sixth embodiment;

FIG. 7C is a schematic diagram of the cutter section in the diathermic cutter according to the sixth embodiment as seen from an arrow 7C direction shown in FIG. 7B;

FIG. 7D is a schematic diagram of the cutter section in the diathermic cutter according to the sixth embodiment as seen from an arrow 7D direction shown in FIG. 7B;

FIG. 8A is a schematic sectional view of the cutter section in the diathermic cutter according to a seventh embodiment;

FIG. 8B is a schematic diagram of the cutter section in the diathermic cutter according to the seventh embodiment;

FIG. 9 is a schematic diagram showing that the diathermic cutter shown in FIG. 8 is used to cut off the lesion mucosa portion;

FIG. 10 is a schematic diagram showing a modified cutter section in the diathermic cutter according to a seventh embodiment;

FIG. 11A is a schematic diagram showing the modified cutter section in the diathermic cutter according to the seventh embodiment;

FIG. 11B is a schematic diagram showing the modified cutter section in the diathermic cutter according to the seventh embodiment;

DETAILED DESCRIPTION OF THE INVENTION

Figure 1A:
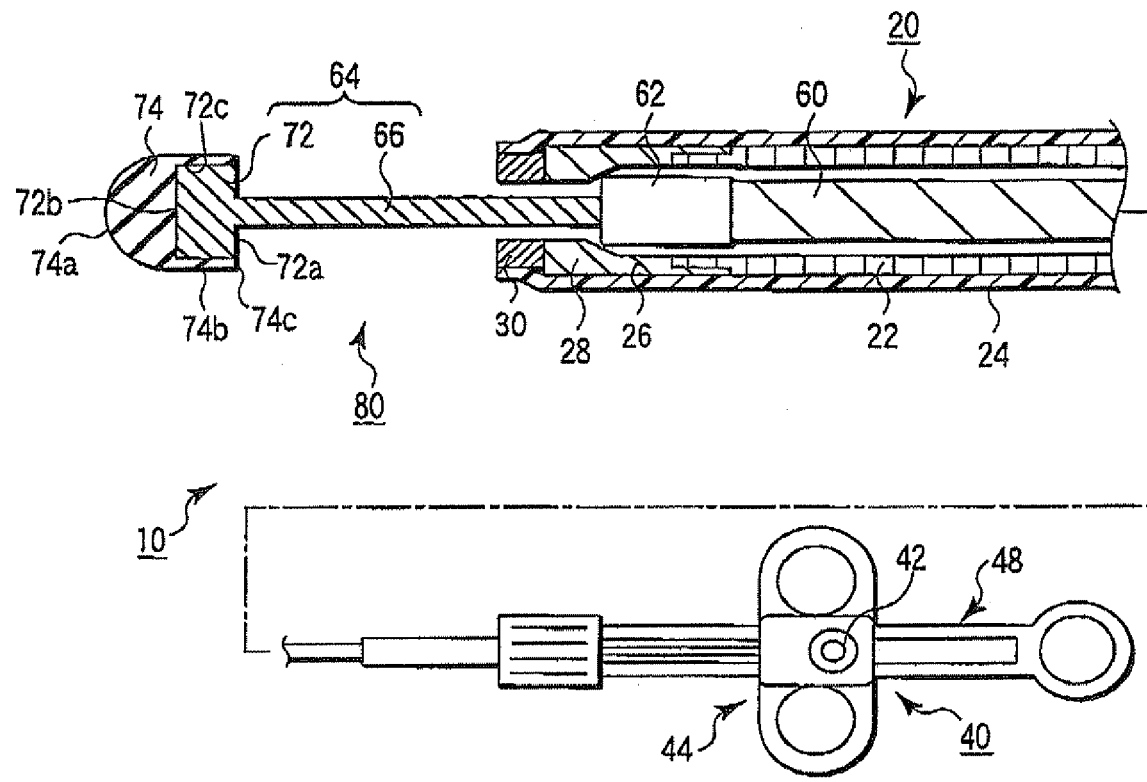
FIG. 1A is a schematic sectional view showing a configuration of a diathermic cutter of a monopolar type according to a first embodiment.
Figure 1B:
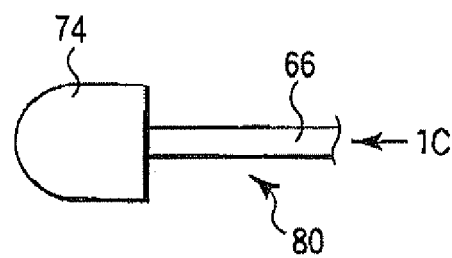
FIG. 1B is a schematic diagram showing the configuration of a cutter section in the diathermic cutter according to the first embodiment.
Figure 1C:
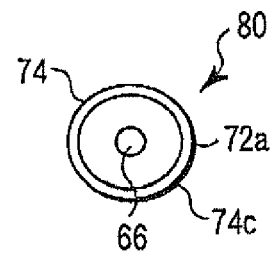
FIG. 1C is a schematic diagram of the cutter section in the diathermic cutter according to the first embodiment as seen from an arrow 1C direction shown in FIG. 1B.

Preferable embodiments of the present invention will hereinafter be described with reference to the drawing.

First, a first embodiment will be described with reference to FIGS. 1A to 2H.

As shown in FIG. 1A, a diathermic cutter 10 according to the present embodiment includes a flexible elongated sheath 20 capable of being inserted in a channel (not shown) of an endoscope as a main body member, and an operating section 40 disposed on a base end of the sheath 20. The sheath 20 includes, for example, a densely wound coil 22, and an insulating tube 24 formed of an insulating material with which an outer periphery of the densely wound coil 22 is coated. The insulating tube 24 is formed, for example, by a tetrafluoroethylene material.

The tip end of the densely wound coil 22 is connected to a cylindrical stopper member 26. The outer peripheral surface of the stopper member 26 is coated with the tip end of the insulating tube 24 on the same plane as that of the outer peripheral surface of the densely wound coil 22. A thickness of the stopper member 26 on the tip-end side is increased inwards in a diametric direction from a base-end side to dispose a thick portion 28 on the inner surface of the stopper member 26. An annular sheath tip-end insulating chip 30 is disposed on the tip-end side of the thick portion 28. The inner peripheral surface of the sheath tip-end insulating chip 30 is substantially on the same plane as that of the inner peripheral surface of the thick portion 28. The outer peripheral surface of the sheath tip-end insulating chip 30 is coated with the insulating tube 24.

The operating section 40 of the diathermic cutter 10 includes an operating section main body 48 and a slider 44 for operation slidable on the operating section main body 48. The slider 44 for operation includes a connector section 42 electrically connected to a cord (not shown) leading to a high-frequency generation device (not shown).

A conductive operating wire 60 is inserted through the sheath 20. The base end of the operating wire 60 is connected to the slider 44 for operation. A conductive stopper receiving section 62 which abuts on the stopper member 26 is attached to the tip end of the operating wire 60.

The stopper receiving section 62 on the tip end of the operating wire 60 is connected to a cutter section 80. The cutter section 80 includes an electrode 64, and an electrically insulating member 74 disposed on the tip end of the electrode 64.

The electrode 64 includes a small-diameter electrode section 66 and a large-diameter electrode section 72. The small-diameter electrode section 66 is a projected member (an elongated member) capable of projecting in an axial direction with respect to the tip end of the sheath 20. The large-diameter electrode section 72 is a sideward extending section disposed on the tip end of the small-diameter electrode section 66 and extended sideward with respect to the axial direction of the small-diameter electrode section 66. The small-diameter electrode section 66 is formed by a conductive material, and is electrically connected to the stopper receiving section 62. Therefore, the small-diameter electrode section 66 is electrically connected to the connector section 42 of the slider 44 for operation via the stopper receiving section 62 and operating wire 60, and is movable along the axial direction in an inner hole of the sheath 20 by an advance/retreat operation of the operating wire 60. Therefore, the small-diameter electrode section 66 is capable of projecting/retrojecting with respect to the tip end of the sheath 20.

The large-diameter electrode section 72 is formed integrally with the tip end of the small-diameter electrode section 66. Therefore, the large-diameter electrode section 72 is formed by a conductive material in the same manner as in the small-diameter electrode section 66. The large-diameter electrode section 72 is formed in a disc shape extending outwards in the diametric direction of the small-diameter electrode section 66 from the small-diameter electrode section 66 (having a diameter larger than that of the small-diameter electrode section 66).

The electrically insulating member 74 includes a solid tip-end portion 74a having a semispherical outer peripheral surface, and a cylindrical side surface portion 74b having the same outer diameter as that of the tip-end portion 74a. The electrically insulating member 74 including the tip-end portion 74a and side surface portion 74b are formed, for example, by a ceramic material. The large-diameter electrode section 72 is exposed toward the sheath 20 from the electrically insulating member 74, and the surface of the large-diameter electrode section 72 is covered with the electrically insulating member 74. That is, while only a base-end surface (surface disposed opposite to the tip end of the sheath 20) 72a of the large-diameter electrode section 72 is exposed to the outside, a tip-end surface (surface on a side opposite to that of the base-end surface) 72b and a circumferential side surface portion 72c of the large-diameter electrode section 72 are completely covered with the electrically insulating member 74. A base end 74c of the electrically insulating member 74 is formed on the same plane as that of the base-end surface 72a of the large-diameter electrode section 72.

Next, a function of the diathermic cutter 10 according to the present embodiment will be described. First, an operation of the diathermic cutter 10 will be described.

The slider 44 for operation and operating section main body 48 of the operating section 40 are grasped, and the slider 44 for operation is moved rearwards (on the base-end portion side) with respect to the operating section main body 48. The operating wire 60 moves rearwards, the small-diameter electrode section 66 is accordingly drawn into the sheath 20, and the base-end surface 72a of the large-diameter electrode section 72 abuts on the tip end of the sheath 20. When the cutter section 80 is not used at the time of insertion of the endoscope into the channel, the diathermic cutter 10 is mainly in this state.

The slider 44 for operation is moved forwards (on the tip-end side) with respect to the operating section main body 48. The operating wire 60 moves forwards together with the slider 44 for operation, accordingly the small-diameter electrode section 66 projects outwards from the tip end of the sheath 20, and the base-end surface 72a of the large-diameter electrode section 72 is isolated from the tip end of the sheath 20 on a front side. The diathermic cutter 10 is used in this state, when power is supplied to the cutter section 80 to cut off the mucosa.

Next, an operation of cutting off the mucosa in a body cavity, for example, via an endoscope by use of the diathermic cutter 10 will be described with reference to FIGS. 2A to 2H.

A needle for syringe (not shown) is introduced into the body cavity through the endoscope (not shown). Physiological saline is injected in a mucosa lower layer of a lesion mucosa portion 90 which is a target portion to be cut off in the body cavity, and the lesion mucosa portion 90 is raised.

An opposite pole (not shown) is attached to a patient. A diathermic cutter 92 (e.g., see Jpn. Pat. Appln. KOKAI Publication No. 4-329944) including a known needle-shaped electrode (cutter section) is similarly endoscopically introduced. Initial incision is carried out to make a hole 94 in a part of the mucosa around the lesion mucosa portion 90 with the diathermic cutter 92 (see FIG. 2A).

The diathermic cutter 10 of the present embodiment is similarly introduced into the body cavity via the channel of the endoscope in a state in which the cutter section 80 is drawn into the sheath 20. The cutter section 80 of the diathermic cutter 10 is projected from the tip end of the endoscope (see FIG. 2B). The cutter section 80 of the diathermic cutter 10 is inserted into the initially incised hole 94 (see FIG. 2C).

While a high-frequency current is supplied to the electrode 64 (small-diameter electrode section 66 and large-diameter electrode section 72) of the cutter section 80, the cutter section 80 of the diathermic cutter 10 is moved along a predetermined cut-off direction as shown in FIGS. 2D and 2E. When the cutter section 80 is moved in a transverse direction (lateral direction of the small-diameter electrode section 66), the mucosa contacting the small-diameter electrode section 66 is cut open by the small-diameter electrode section 66.

When the cutter section 80 is not easily moved in the transverse direction, as shown in FIGS. 2F and 2G, the cutter section 80 is moved in a vertical direction (axial direction of the small-diameter electrode section 66). The mucosa lifted up by the large-diameter electrode section 72 is cut open by the exposed base-end surface 72a of the large-diameter electrode section 72. The movement of the transverse direction is combined with that of the vertical direction to move the cutter section 80, and the lesion mucosa portion 90 is accordingly cut open over a peripheral direction.

All surface portions of the large-diameter electrode section 72 excluding the base-end surface 72a (tip-end surface 72b and circumferential side surface portion 72c) are covered with the electrically insulating member 74. Even if the tip end of the cutter section 80 contacts a non-cut-off tissue by the movement of the cutter section 80 in the axial direction, the high-frequency current supplied to the large-diameter electrode section 72 does not flow through the non-cut-off tissue, due to the insulating function of the electrically insulating member 74. Therefore, the operator does not have to perform a laborious operation of moving the cutter section 80 in a specific depth in such a manner that the non-cut-off tissue positioned in a deep part of a cut-off object portion does not contact the cutter section 80.

As described above, the lesion mucosa portion 90 is completely cut open over the peripheral direction. As shown in FIG. 2H, the small-diameter electrode section 66 and the base-end surface 72a of the large-diameter electrode section 72 abut on a cut area obtained by cutting open the periphery of periphery of the lesion mucosa portion 90, the movement of the diathermic cutter 10 in the transverse direction is combined with that in the vertical direction, and the lesion mucosa portion 90 is successively cut open and peeled by the small-diameter electrode section 66 and the large-diameter electrode section 72. After cutting off all of the lesion mucosa portion 90, the lesion mucosa portion 90 is grasped with grasping forceps (not shown), and is taken out via the endoscope to end the treatment.

As described above, the following effect is obtained by the diathermic cutter 10 of the present embodiment.

The diathermic cutter 10 includes the sheath 20 having electrically insulating properties as a main body member, the small-diameter electrode section 66 which is a projected member (an elongated member) projecting in the axial direction from the tip end of the sheath 20, and the large-diameter electrode section 72 which is a sideward extending section disposed on the tip-end side of the small-diameter electrode section 66 and extending in the lateral direction of the small-diameter electrode section 66. Therefore, not only when the cutter section 80 is moved in the transverse direction in order to cut off the lesion mucosa portion 90 but also when the cutter section 80 is moved in various directions including the axial direction so as to lift up the mucosa by the large-diameter electrode section 72, the incision can be made. Therefore, movement directions in which the incision is possible (degree of freedom in an incision direction) remarkably increase as compared with a case where only the small-diameter electrode section 66 is used. Then, an incision operation of the lesion mucosa portion 90 can diversely and easily be carried out.

The diathermic cutter 10 of the present embodiment includes the electrically insulating member 74 from which the large-diameter electrode section 72 is exposed toward the sheath 20 and with which the surface of the large-diameter electrode section 72 is covered. Therefore, when the lesion mucosa portion 90 is cut open, the operator does not have to carry out the laborious operation of advancing/retreating/operating the cutter section 80 in a specific axial direction range in which the non-cut-off tissue positioned in the depth of the cut-off object portion does not contact the cutter section 80. Therefore, the incision operation of the lesion mucosa portion 90 can electrically, safely, and easily be carried out.

In the diathermic cutter 10 of the present embodiment, the large-diameter electrode section 72 is formed in a disc shape in which the small-diameter electrode section 66 is an axis. Therefore, the lesion mucosa portion 90 can be cut off without aligning the specific portion of the cutter section 80 in the incision direction.

Next, a second embodiment will be described with reference to FIGS. 3A and 3B. This embodiment is a modification of the first embodiment, the same members as those described in the first embodiment are denoted with the same reference numerals, and detailed description is omitted. Hereinafter, this also applies to third to ninth embodiments.

Figure 3A:
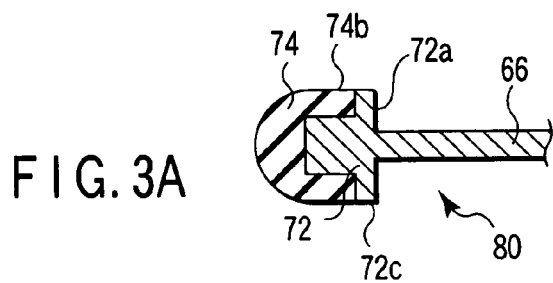
FIG. 3A is a schematic sectional view of the cutter section in the diathermic cutter according to a second embodiment.
Figure 3B:
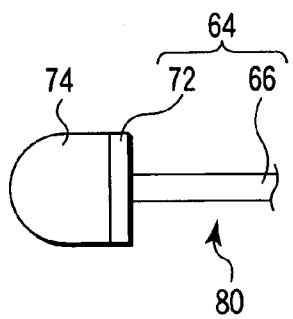
FIG. 3B is a schematic diagram of the cutter section in the diathermic cutter according to the second embodiment.

As shown in FIGS. 3A and 3B, for the cutter section 80 of the present embodiment, the circumferential side surface portion 72c of the large-diameter electrode section 72 is formed on the same plane as that of the side surface portion 74b of the electrically insulating member 74. That is, the circumferential side surface portion 72c of the large-diameter electrode section 72 is exposed. The cutter section 80 of the present embodiment is different from that described in the first embodiment only in this respect.

Next, the function of the diathermic cutter 10 of the present embodiment will be described. It is to be noted that the description of the same function as that described in the first embodiment is omitted.

After completely cutting open the lesion mucosa portion 90 over the peripheral direction, the small-diameter electrode section 66 and the base-end surface 72a and circumferential side surface portion 72c of the large-diameter electrode section 72 abut on the cut area obtained by cutting open the periphery of the lesion mucosa portion 90. The movement of the diathermic cutter 10 in the transverse direction is combined with that in the vertical direction to successively cut open and peel the lesion mucosa portion 90 by the small-diameter electrode section 66 and large-diameter electrode section 72.

As described above, the following effect is obtained by the diathermic cutter 10 of the present embodiment. The description of the same effect as that described in the first embodiment will be described.

Since the side surface portion 74b of the electrically insulating member 74 is on the same plane as that of the circumferential side surface portion 72c of the large-diameter electrode section 72, the lesion mucosa portion 90 can be cut open also by this portion (circumferential side surface portion 72c). Therefore, the incision of the transverse direction can be made together with the small-diameter electrode section 66. Therefore, incising properties of the transverse direction can be enhanced, and time can be reduced in peeling the lesion mucosa portion 90.

Figure 4A:
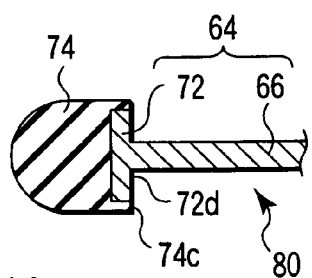
FIG. 4A is a schematic sectional view of the cutter section in the diathermic cutter according to a third embodiment.
Figure 4B:
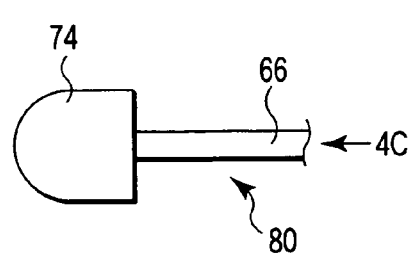
FIG. 4B is a schematic diagram of the cutter section in the diathermic cutter according to the third embodiment.

Next, a third embodiment will be described with reference to FIGS. 4A to 4C.

Figure 4C:
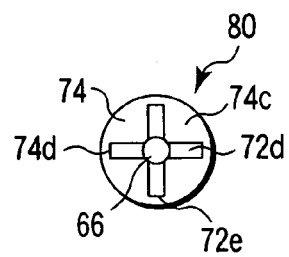
FIG. 4C is a schematic diagram of the cutter section in the diathermic cutter according to the third embodiment as seen from an arrow 4C direction shown in FIG. 4B.

As shown in FIG. 4C, the large-diameter electrode section 72 of the cutter section 80 of the present embodiment is exposed in a radial shape or a cross shape here in a direction crossing at right angles to the axial direction of the small-diameter electrode section 66 in the base-end surface 72a. The portion other than the base end of the large-diameter electrode section 72 is covered with the electrically insulating member 74.

A cross-shaped base end 72d of the large-diameter electrode section 72 is formed on the same plane as that of the base end 74c of the electrically insulating member 74. A thick portion 74d of the electrically insulating member 74 is disposed in a distant position 72e radially distant from a central portion of the cross-shaped portion, and the distant position is drawn inwards with respect to the outer periphery of the electrically insulating member 74.

Since the function of the diathermic cutter 10 of the present embodiment is the same as that described in the first embodiment, the description is omitted.

As described above, the following effect is obtained by the diathermic cutter 10 of the present embodiment. It is to be noted that the description of the same effect as that of the first embodiment is omitted.

Since an exposed area of the base end is smaller than that of the large-diameter electrode section 72 described in the first embodiment, an output can be concentrated on the exposed portion.

Next, a fourth embodiment will be described with reference to FIGS. 5A to 5C.

Figure 5A:
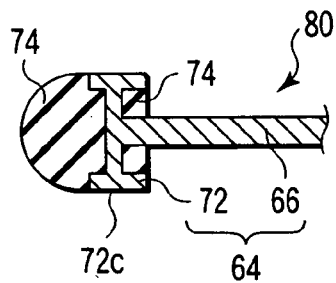
FIG. 5A is a schematic sectional view of the cutter section in the diathermic cutter according to a fourth embodiment.
Figure 5B:
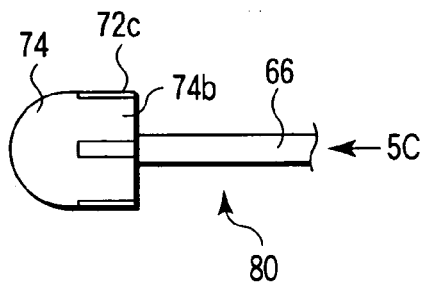
FIG. 5B is a schematic diagram of the cutter section in the diathermic cutter according to the fourth embodiment.
Figure 5C:
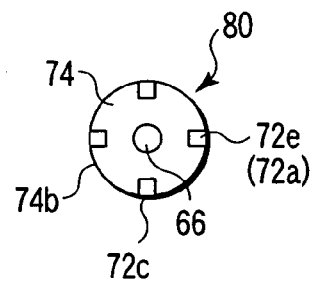
FIG. 5C is a schematic diagram of the cutter section in the diathermic cutter according to the fourth embodiment as seen from an arrow 5C direction shown in FIG. 5B.

As shown in FIGS. 5A to 5C, the large-diameter electrode section 72 of the cutter section 80 of this embodiment is radially formed in a direction crossing at right angles to the axial direction of the small-diameter electrode section 66. The large-diameter electrode section 72 is formed in the cross shape here. In the base end 72a of the large-diameter electrode section 72, a distant position 72e distant from the small-diameter electrode section 66, that is, only a side edge of the large-diameter electrode section 72 is exposed to the outside, and the other portion of the large-diameter electrode section is covered with the electrically insulating member 74 on the same plane as that of the exposed portion. The circumferential side surface portion 72c of the large-diameter electrode section 72 is exposed in the same position as that of the exposed portion in the base end 72a and on the same plane as that of the side surface portion 74b of the electrically insulating member 74.

Since the function of the diathermic cutter 10 of the present embodiment is the same as that described in the second embodiment, the description is omitted.

As described above, the following effect is obtained by the diathermic cutter 10 of the present embodiment. It is to be noted that the description of the same effect as that of the above-described embodiment is omitted.

Since the exposed area of the base end is smaller than that of the large-diameter electrode section 72 including the cross-shaped portion described in the third embodiment, the output can be concentrated on the exposed portion.

Next, a fifth embodiment will be described with reference to FIGS. 6A to 6C.

Figure 6A:
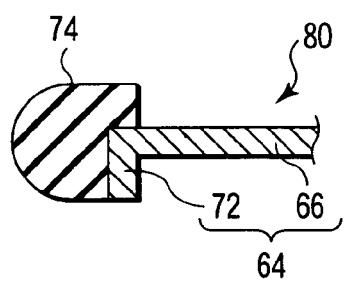
FIG. 6A is a schematic sectional view of the cutter section in the diathermic cutter according to a fifth embodiment.
Figure 6B:
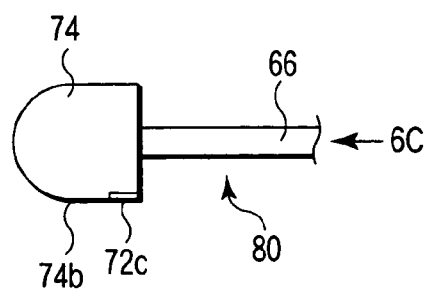
FIG. 6B is a schematic diagram of the cutter section in the diathermic cutter according to the fifth embodiment.
Figure 6C:
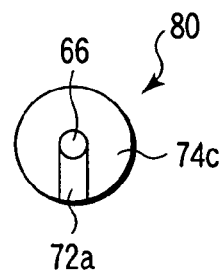
FIG. 6C is a schematic diagram of the cutter section in the diathermic cutter according to the fifth embodiment as seen from an arrow 6C direction shown in FIG. 6B.

As shown in FIGS. 6A to 6C, the large-diameter electrode section 72 of the cutter section 80 in the diathermic cutter 10 of the fifth embodiment extends in one direction crossing at right angles to the axial direction of the small-diameter electrode section 66. That is, the electrode 64 is formed substantially in an L shape. The electrically insulating member 74 is disposed on the tip end of the large-diameter electrode section 72. The base end 72a of the large-diameter electrode section 72 is exposed on the same plane on the base-end side of the electrically insulating member 74. The large-diameter electrode section 72 is formed on the same plane as that of the side surface portion 74b of the electrically insulating member 74 in the distant position 72c of the large-diameter electrode section 72 distant from the small-diameter electrode section 66.

Next, the function of the diathermic cutter 10 of the present embodiment will be described. It is to be noted that the description of the same function as that of the diathermic cutter 10 described in the first embodiment is omitted.

When the base end 72a and circumferential side surface portion 72c of the large-diameter electrode section 72 abut on the lesion mucosa portion 90 to cut open the lesion mucosa portion, the direction of the cutter section 80 is adjusted.

As described above, the following effect is obtained by the diathermic cutter 10 of the present embodiment. It is to be noted that the description of the same effect as that described in the first embodiment is omitted.

Since the electrode 64 is formed substantially in the L shape, and the exposed area of the large-diameter electrode section 72 is smaller than that of the large-diameter electrode section 72 described in the first embodiment, the output can be concentrated on the exposed portion.

Next, a sixth embodiment will be described with reference to FIGS. 7A to 7D.

As shown in FIGS. 7A to 7D, the electrically insulating member 74 of the diathermic cutter 10 of the sixth embodiment is formed substantially in a rectangular parallelepiped shape. The electrode 64 is formed substantially in the L shape. The electrically insulating member 74 is disposed on the tip end of the large-diameter electrode section 72. The electrically insulating member 74 has the same width and thickness as those of the large-diameter electrode section 72. That is, the distant position 72e of the large-diameter electrode section 72 and a peripheral side surface 66a of the small-diameter electrode section 66 are formed on the same plane as that of a thickness surface 74e of the electrically insulating member 74 in the direction crossing at right angles to the small-diameter electrode section 66. A width surface 74f of the electrically insulating member 74 is connected to the large-diameter electrode section 72 on the same plane (without any step).

Since the function of the diathermic cutter 10 of the sixth embodiment is the same as that described in the fifth embodiment, the description is omitted.

As described above, the following effect is obtained by the diathermic cutter 10 of the present embodiment. It is to be noted that the description of the same effect as that of the diathermic cutter 10 of the fifth embodiment is omitted.

Since the electrically insulating member 74 is formed to be smaller than that of the cutter section 80 described in the fifth embodiment, it is easy to abut the electrode 64 on the cut area obtained by cutting open the periphery of the lesion mucosa portion 90, and the cutter section can be adapted for a fine operation.

It is to be noted that for the diathermic cutter 10 of the sixth embodiment, as shown in FIGS. 7A to 7C, the large-diameter electrode section 72 has substantially the same thickness as that of the electrically insulating member 74, but the electrically insulating member 74 may also be formed to be thin, for example, by insulating/coating the tip-end side of the large-diameter electrode section 72.

Next, a seventh embodiment will be described with reference to FIGS. 8A to 11B.

As shown in FIGS. 8A and 8B, the side surface portion 72c of the large-diameter electrode section 72 of the cutter section 80 in the diathermic cutter 10 of the seventh embodiment is slightly projected from the side surface portion 74b of the electrically insulating member 74 outwards in the diametric direction of the small-diameter electrode section 66. Therefore, a part of the tip-end surface 72b of the large-diameter electrode section 72 is exposed forwards.

Next, the function of the diathermic cutter 10 of the seventh embodiment will be described. It is to be noted that the description of the same function as that described in the fifth embodiment is omitted.

After completely cutting open the lesion mucosa portion 90 over the peripheral direction, as shown in FIG. 9, the small-diameter electrode section 66 and the large-diameter electrode section 72 abut on the cut area obtained by cutting open the periphery of the lesion mucosa portion 90. The movement of the diathermic cutter 10 in the transverse direction is combined with that in the vertical direction to successively cut open and peel the lesion mucosa portion 90 by the small-diameter electrode section 66 and large-diameter electrode section 72. Furthermore, the large-diameter electrode section 72 is pressed in the vertical direction to cut open the lesion mucosa portion 90.

As described above, the following effect is obtained by the diathermic cutter 10 of the present embodiment. It is to be noted that the description of the same effect as that described in the fifth embodiment is omitted.

Since the side surface portion 72c of the large-diameter electrode section 72 projects from the side surface portion 74b of the electrically insulating member 74 outwards in the diametric direction, the lesion mucosa portion 90 can be cut open even in this projecting portion. At least a part of the tip-end surface 72b of the large-diameter electrode section 72 is exposed forwards. Therefore, when the large-diameter electrode section 72 is pressed against the lesion mucosa portion 90 in the vertical direction, the lesion mucosa portion 90 can be cut open by the large-diameter electrode section 72.

It is to be noted that an example in which the side surface portion 72c of the large-diameter electrode section 72 of the cutter section 80 projects from the side surface portion 74b of the electrically insulating member 74 is not limited to the example shown in FIGS. 8A and 8B. The example shown in FIGS. 10 to 11B may also be used.

In FIG. 10, the electrode 64 is formed substantially in the L shape. The electrically insulating member 74 is disposed on the tip end of the small-diameter electrode section 66 on the tip-end side of the large-diameter electrode section 72 without interfering with the large-diameter electrode section 72. That is, the tip-end surface 72b of the large-diameter electrode section 72 is exposed on the tip-end side.

In FIGS. 11A and 11B, the electrode 64 is formed substantially in a T shape. The electrically insulating member 74 is disposed on the tip end of the electrode 64 in the same manner as in FIG. 10. Furthermore, in FIG. 11B, the large-diameter electrode section 72 is formed asymmetrically with respect to a central axis 66b of the small-diameter electrode section 66, that is, in different lengths.

In the mode shown in FIG. 11B, when the portions having different lengths in the large-diameter electrode section 72 are selectively used, an incision amount (depth) can be adjusted.

Next, an eighth embodiment will be described with reference to FIGS. 12A and 12B.

Figure 12A:
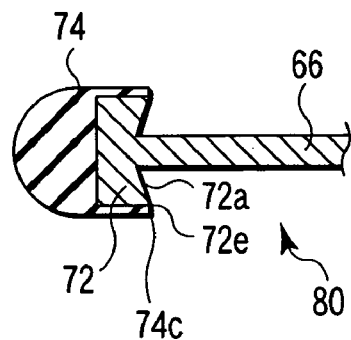
FIG. 12A is a schematic sectional view of the cutter section in the diathermic cutter according to an eighth embodiment.
Figure 12B:
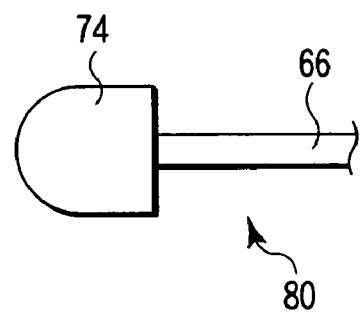
FIG. 12B is a schematic diagram of the cutter section in the diathermic cutter according to the eighth embodiment.

As shown in FIG. 12A, the base end 72a of the large-diameter electrode section 72 of the cutter section 80 in the diathermic cutter 10 of the eighth embodiment is formed in an earthenware mortar shape. The distant position 72e of the base end 72a of the large-diameter electrode section 72 distant in a direction crossing at right angles to the small-diameter electrode section 66 is formed on the same plane as that of the base end 74c of the electrically insulating member 74.

Since the function and effect of the diathermic cutter 10 of the eighth embodiment are the same as those of the diathermic cutter 10 of the first embodiment, the description is omitted.

Next, a ninth embodiment will be described with reference to FIG. 13.

Figure 13:
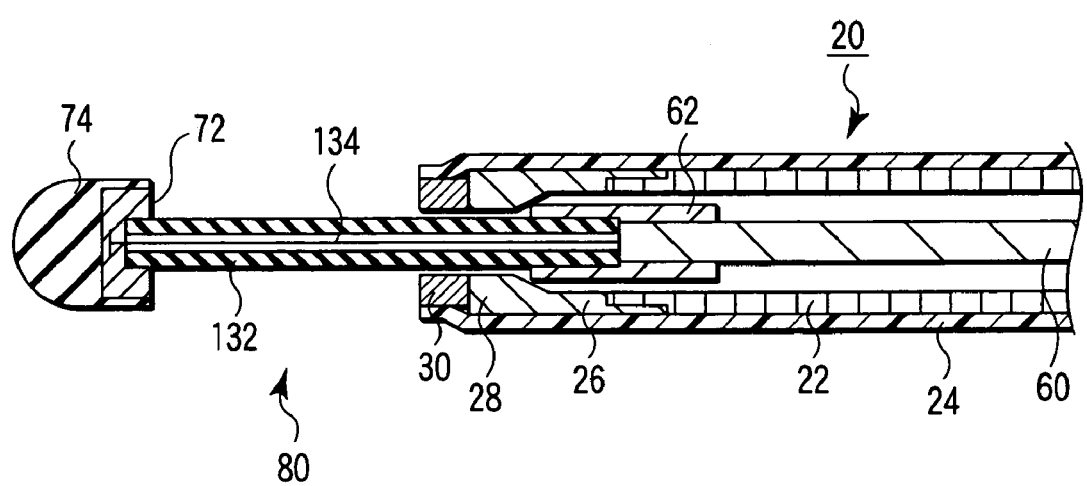
FIG. 13 is a schematic sectional view showing a configuration of the monopolar type diathermic cutter on a tip-end side according to a ninth embodiment.

As shown in FIG. 13, a small-diameter cylindrical member 132 having electrically insulating properties is attached to the tip end of the operating wire 60 in the diathermic cutter 10 of the ninth embodiment, that is, the stopper receiving section 62. A conductive wire 134 connected to the operating wire 60 is inserted in an inner hole of the cylindrical member 132. The tip end of the conductive wire 134 is electrically connected to the large-diameter electrode section 72 formed in a columnar shape. The large-diameter electrode section 72 is coated with the electrically insulating member 74 similar to that of the first embodiment.

The cylindrical member 132 cooperates with the operating wire 60 to slide against the sheath 20, and has a function of a retrojectable projecting member with respect to the tip end of the sheath 20. For the cutter section 80 described in the present embodiment, the projecting member is not formed as the electrode.

Next, the function of the diathermic cutter 10 of the present embodiment will be described. It is to be noted that the description of the same function as that of the diathermic cutter 10 of the first embodiment is omitted.

While the high-frequency current is supplied to the large-diameter electrode section 72 of the cutter section 80, the cutter section 80 of the diathermic cutter 10 is moved as shown in FIGS. 2F and 2G. Moreover, the large-diameter electrode section 72 is lifted up with respect to the mucosa to cut open the mucosa. The periphery of the lesion mucosa portion 90 is cut open in this manner.

As described above, the following effect is obtained by the diathermic cutter 10 of the ninth embodiment. It is to be noted that the description of the same effect as that of the diathermic cutter 10 of the first embodiment is omitted.

Since the cylindrical member 132 is not disposed as the small-diameter electrode section, electrical energy can be concentrated on the large-diameter electrode section 72.

It is to be noted that the shape of the large-diameter electrode section 72 of the cutter section 80 including the projecting member having the electrically insulating properties is not limited to that shown in FIG. 13, and the large-diameter electrode section may also preferably have the shape of the large-diameter electrode section 72 of the cutter section 80 described, for example, in the second to eighth embodiments.

Next, a tenth embodiment will be described with reference to FIG. 14. The same members as those used in the diathermic cutter 10 of the first to ninth embodiments are denoted with the same reference numerals, and detailed description is omitted.

Figure 14:
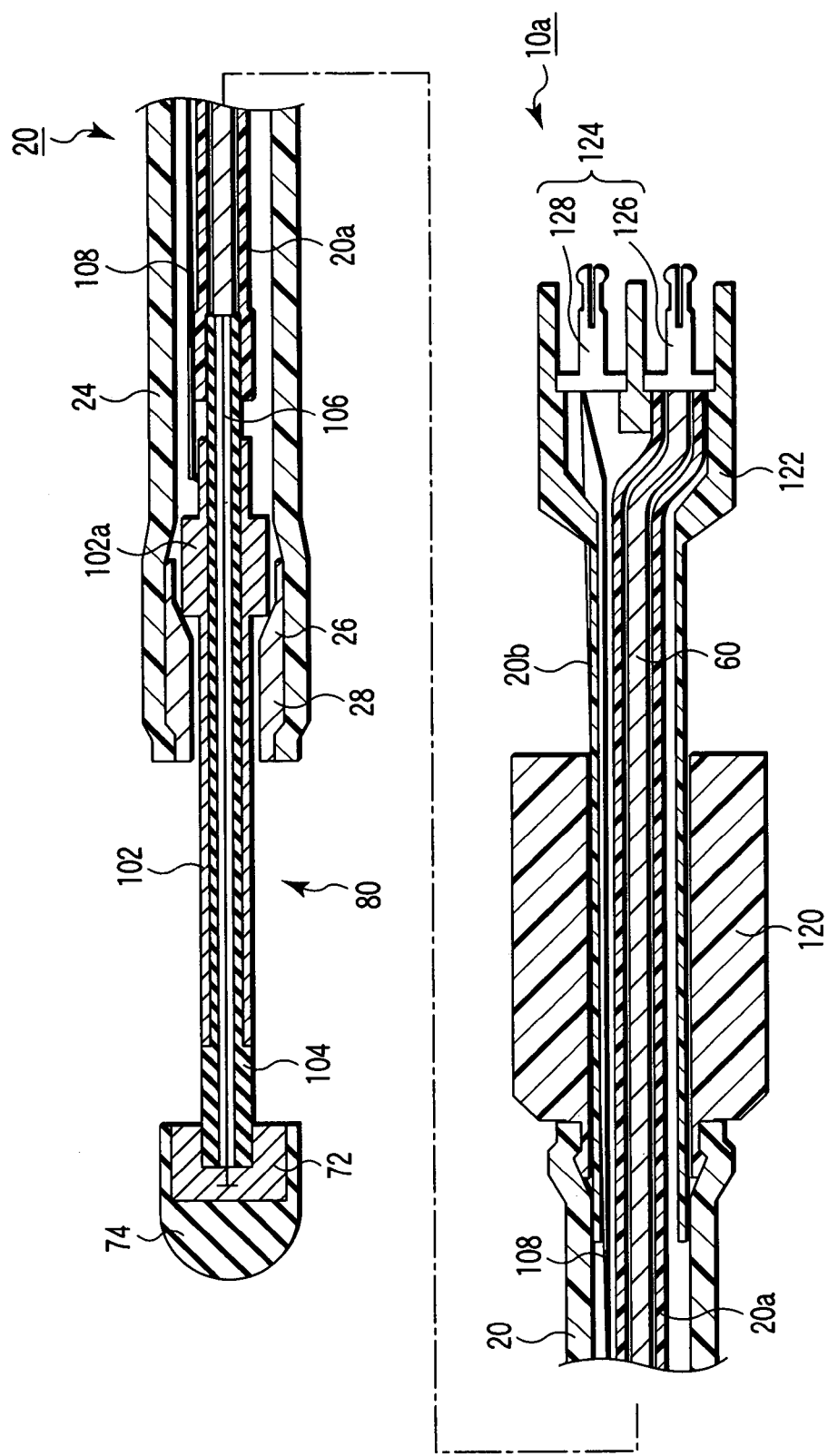
FIG. 14 is a schematic sectional view showing the configuration of a bipolar type diathermic cutter according to a tenth embodiment.

As shown in FIG. 14, the cylindrical stopper member 26 is disposed on the tip end of the sheath 20 formed of the electrically insulating tube 24 of a diathermic cutter 10a of the tenth embodiment. On the inner surface of the stopper member 26, the thick portion 28 is formed by increasing the thickness of the stopper member 26 on the tip-end side inwards in the diametric direction on the base-end side. A hard and cylindrical holding section 120 having substantially the same diameter as that of the inner hole of the sheath 20 is attached to the base end of the sheath 20.

The cutter section 80 of the diathermic cutter 10a is constituted as follows. The small-diameter electrode section includes a first cylindrical member 102 having conductivity and small diameter, a second cylindrical member 104 having the electrically insulating properties, and a first conductive line 106. A stopper receiving section 102a is formed by enlarging the diameter of the vicinity of the base end of the first cylindrical member 102. The stopper receiving section 102a is engaged with the thick portion 28 of the stopper member 26. The second cylindrical member 104 is disposed on an inner peripheral side of the first cylindrical member 102. The second cylindrical member 104 extends forwards from the tip end of the first cylindrical member 102 and rearwards from the base end. The vicinity of the tip end of the second cylindrical member 104 is formed to be thick outwards in the diametric direction from the base end, and is formed on the same plane as that of the outer peripheral surface of the first cylindrical member 102.

The operating wire 60 is inserted through the sheath 20. The outer periphery of the operating wire 60 is coated with an electrically insulating tube 20a. The tip end of the electrically insulating tube 20a is connected to the base end of the second cylindrical member 104. The first conductive line 106 connected to the operating wire 60 is inserted through the second cylindrical member 104. The large-diameter electrode section 72 formed in the columnar shape is disposed on the tip end of the second cylindrical member 104. The large-diameter electrode section 72 is electrically connected to the first conductive line 106. The large-diameter electrode section 72 is coated with the electrically insulating member 74. The electrically insulating member 74 is formed in a semispherical shape on the tip-end side, and is formed in a cylindrical shape having the same outer diameter as that of the semispherical portion on the base-end side. The base end of the large-diameter electrode section 72 is formed on the same plane as that of the base-end surface 72a of the base end of the electrically insulating member 74.

The base end of the first cylindrical member 102 is electrically connected to the tip end of a second conductive line 108 extending rearwards through the inner hole of the sheath 20. Therefore, the first cylindrical member 102 has a function of the small-diameter electrode section.

It is to be noted that the second conductive line 108 is isolated from the operating wire 60 connected to the first conductive line 106 by the electrically insulating tube 20a. Therefore, the large-diameter electrode section 72 is not electrically connected to the small-diameter electrode section including the first cylindrical member 102 in a non-conductive state.

The holding section 120 includes a hard operating pipe 20b capable of advancing/retreating in the axial direction and formed of the electrically insulating material. The base end of the operating pipe 20b extends further from the base end of the holding section 120 to form a grasping section 122. A connector portion 124 is disposed in the grasping section 122. The connector portion 124 includes a first connector portion 126 connected to the base end of the operating wire 60, and a second connector portion 128 connected to the second conductive line 108.

Next, the function of the diathermic cutter 10a of the tenth embodiment will be described. It is to be noted that the description of the same function as that of the diathermic cutter 10 of the first embodiment is omitted.

First, the operation of the diathermic cutter 10a will be described. The grasping section 122 is slid in the vicinity of the holding section 120. The operating wire 60, electrically insulating tube 20a, and second conductive line 108 cooperate with one another to slide, and the first and second cylindrical members 102, 104 project from the tip end of the sheath 20. The diathermic cutter 10a is used in this state, when cutting off the lesion mucosa portion 90.

Conversely, the grasping section 122 is slid in a direction distant from the holding section 120. The first and second cylindrical members 102, 104 are drawn inside the sheath 20.

In an actual treatment, both the large-diameter electrode section 72 and the first cylindrical member 102 abut on the lesion mucosa portion 90. While the high-frequency current is supplied via the connector portion 124 in this state, the cutter section 80 is moved to cut open and peel the lesion mucosa portion 90. A way of moving the cutter section 80 is the same as that described in the first embodiment.

As described above, the following effect is obtained by the diathermic cutter 10a of the tenth embodiment. It is to be noted that the description of the same effect as that of the diathermic cutter 10 of the first embodiment is omitted.

The diathermic cutter 10a includes a bipolar constitution which is capable of cutting open the lesion mucosa portion 90 positioned between the large-diameter electrode section 72 and the first cylindrical member 102 (small-diameter electrode section) between which a current is locally supplied. Therefore, an electrical influence on a living body (patient) can be reduced. Different from the monopolar constitution of the above-described embodiments, the opposite pole plate is not required.

It is to be noted that the shape of the large-diameter electrode section 72 disposed inside the electrically insulating member 74 is not limited to the above-described shape, and the constitution described, for example, in the first to ninth embodiments may also be used. A distance between the base end of the large-diameter electrode section 72 and the tip end of the first cylindrical member 102 is preferably appropriately formed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A monopolar diathermic cutter comprising:
a cylindrical main body member including a tip end portion, the tip end portion having electrically insulating properties;
an elongated member including a central axis and a tip end projecting from the tip end portion of the main body member, the elongated member being movably inserted in the main body member;
an electrode disposed on the tip end of the elongated member such that the electrode faces the tip end portion of the main body member, extending in a direction deviating from the central axis of the elongated member, and including a base-end surface disposed opposite to the tip end potion of the main body member; and
an electrically insulating member with which the electrode is coated in such a manner that at least a part of the base-end surface of the electrode is exposed, wherein:

the elongated member has electrically conductive properties, the electrode is electrically connected to the elongated member to form a single electrode member, and wherein the electrode extending in the direction deviating from the central axis of the elongated member includes a proximal end with respect to the central axis of the elongated member, and the proximal end of the electrode is located inward of and connected to a side surface of the electrically insulating member.

2. A monopolar diathermic cutter comprising:
a cylindrical main body member including a tip end portion, the tip end portion having electrically insulating properties;
an elongated member including a central axis and a tip end projecting from the tip end portion of the main body member, the elongated member being movably inserted in the main body member;
an electrode disposed on the tip end of the elongated member such that the electrode faces the tip end portion of the main body member, extending in a direction deviating from the central axis of the elongated member, and including a base-end surface disposed opposite to the tip end portion of the main body member; and
an electrically insulating member with which the electrode is coated in such a manner that at least a part of the base-end surface of the electrode is exposed, wherein:

the elongated member has electrically conductive properties, the electrode is electrically connected to the elongated member to form a single electrode member, and the electrode extending in the direction deviating from the central axis of the elongated member includes a proximal end with respect to the central axis of the elongated member, and the proximal end of the electrode at least partially projects further outwards than a side surface of the electrically insulating member.

* * * * *